United States Patent [19]

Ray et al.

[11] Patent Number: 4,800,903

[45] Date of Patent: Jan. 31, 1989

[54] NICOTINE DISPENSER WITH POLYMERIC RESERVOIR OF NICOTINE

[76] Inventors: Jon P. Ray, 12544 Judson Rd., San Antonio, Tex. 78233; James E. Turner, 307 Wayside, San Antonio, Tex. 78213; Michael P. Ellis, 811 River Rd., San Antonio, Tex. 78212; Ronald G. Oldham, 1410 Tarton, San Antonio, Tex. 78231

[21] Appl. No.: 738,120

[22] Filed: May 24, 1985

[51] Int. Cl.⁴ .................... A24D 1/00; A24D 3/08; A24F 1/00
[52] U.S. Cl. .................... 131/273; 131/270; 131/335; 128/202.21
[58] Field of Search ............... 131/332, 270, 273, 331, 131/335, 343, 341; 128/202.21

[56] References Cited

U.S. PATENT DOCUMENTS

| | | | |
|---|---|---|---|
| 3,229,008 | 1/1966 | Harrington et al. | 131/343 |
| 3,393,685 | 7/1968 | Mumpowes et al. | 131/341 |
| 4,189,511 | 2/1980 | Levers et al. | 131/332 |

FOREIGN PATENT DOCUMENTS 2149190  4/1978  Fed. Rep. of Germany .

*Primary Examiner*—V. Millin
*Attorney, Agent, or Firm*—Arnold, White & Durkee

[57] ABSTRACT

A nicotine dispenser comprising a polyolefin porous plug with reversibly retained nicotine therein. The dispenser is mounted in a tubular configuration to provide a cigarette-shaped product adapted to dispense nicotine vapor when air is drawn therethrough. The polymeric reservoir of nicotine comprises a polyolefin, preferably polyethylene or polypropylene, which reversibly absorbs nicotine.

39 Claims, 1 Drawing Sheet

U.S. Patent     Jan. 31, 1989     4,800,903
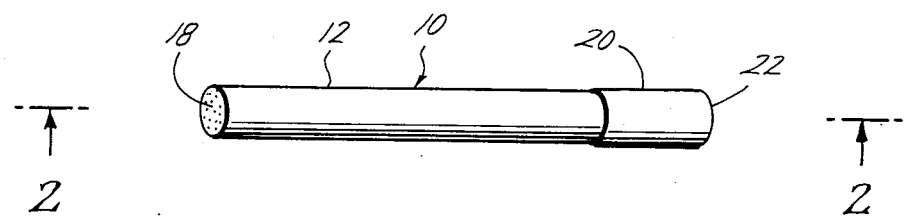
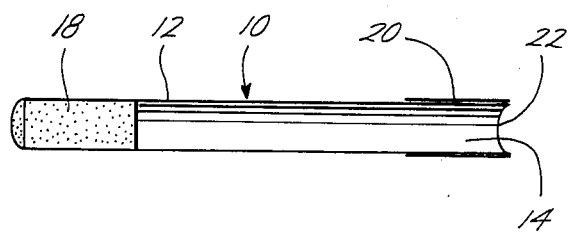

NICOTINE DISPENSER WITH POLYMERIC RESERVOIR OF NICOTINE

BACKGROUND OF THE INVENTION

This invention relates to non-combustible nicotine dispensing devices designed to reduce or eliminate the disadvantages associated with conventional smoking habits.

Nicotine is a toxic liquid alkaloid having the formula $C_5H_4NC_4H_7NCH_3$. When nicotine is obtained from tobacco, as by chewing, sniffing or smoking the substance, the amount of nicotine absorbed into the body generally does not build up to a harmful dose, but produces certain pleasurable effects, frequently leading to habitual use.

One of the most popular versions of nicotine use involves the smoking of cigarettes. When the tobacco in a conventional cigareete is ignited, the combustion of the processed tobacco leaves within the cigarette causes the release of vaporous nicotine, which is drawn through the cigarette and into the user's mouth and lungs when the user sucks or inhales air through the cigarette.

The relative mildness of a cigarette, as compared to a pipe or cigar, permits a user to draw the smoke from the burning cigarette directly into the lungs. Nicotine vapors in the cigarette smoke are rapidly assimilated into the bloodstream of the user from the lungs, so that cigarette smoking provides a method by which a user may very quickly feel the effects of the nicotine.

Although nicotine can be readily introduced into the body through cigarette smoking, the combustion of the tobacco, with the consequent elevated temperatures required in this process, unfortunately results in a number of undesirable consequences associated with smoking combustible cigarettes. Of primary concern are the serious health hazards thought by many to result from smoking combustible cigarettes. The nicotine content of a cigarette is not believed to cause any serious adverse long-term health effects on the human body. Other components, however, are present in tobacco smoke which are thought by many to be harmful. Some of these other components, for example, appear to be carcinogenic.

Furthermore, the smoking of combustible cigarettes may pose a significant fire hazard. Many first which have occurred both within buildings or in natural environments have been attributed to carelessly discarded burning cigarettes. In addition, substantial economic losses may be attributed to smoking, including, for example, significant damage to business and personal property resulting from burns in clothing, carpeting, furniture, etc. caused by stray ashes from cigarettes. Cigarette smoking has also become increasingly objectionable because of the discomfort it may cause to non-smokers who are exposed to the smoke and odor produced by practitioners of the smoking habit.

Because of these undesirable side effects of conventional cigarette smoking, attempts have been made from time to time to provide acceptable substitutes. Such substitutes for combustible cigarette smoking eliminate or ameliorate some or all of the adverse consequences mentioned above. Tobacco concentrates, for example, have been processed into a tablet form which may be sucked or chewed, the nicotine being absorbed into the user's body through the lining of the mouth and digestive system. Such a tablet, of course, does not provide the user with the feel of a cigarette held between the lips.

Furthermore, a tablet-type smoking substitute cannot provide the user with an opportunity to draw air and vapors into the mouth nor inhale the air and vapors into the lungs, these actions being a part of the convetional smoking habit. These actions or activities constitute an important aspect of the psychological and physiological affinities which a smoker acquires for the habit. Without an effective substitute for such smoking activities, a smoking substitute is less likely to satisfy the user and may thus result in a return to combustible cigarette smoking.

An important step forward in the development of a smoking substitute is described in U.S. Pat. No. 4,284,089 to Ray, assiged to the assignee of the present invention and incorporated by reference herein. In this patent a smokeless device for dispensing nicotine is described which may take the appearance of a conventional smoking item, such as a cigarette. Moreover, the device disclosed in the patent enables nicotine to be dispensed in response to users actions that closely simulates conventional smoking activity.

In an illustrated embodiment, the Ray patent discloses a device having the general configuration of a cigarette. However, the exterior of the device defines a gas flow passageway with a flow restriction. The flow restriction is defined by an absorbent material carrying a nicotine solution on the material. In response to the fluid velocity developed at the restriction, nicotine is vaporized from the absorbent material and inhaled by the user. As a result, the user attains a nicotine induced sensation quite similar to that obtained by smoking conventional cigarettes.

While it may be safely posited that the Ray patent represents a pioneering advance in the art, the invenfors of the present invention have appreciated that it would be desirable to optimize the performance of a device of the general type disclosed in the Ray patent. In one aspect, for example, the present inventors have appreciated that it would be highly desirable to increase the amount of nicotine that is vaporized in response to a given puff on such a device.

It is also very important in a nicotine dispenser of this kind to effeciently vaporize the nicotine. Liquid nicotine has an extremely bitter, almost caustic taste. Thus, it is important to dispense the nicotine in a fashion which encourages controlled vaporization while preventing inadvertent suction of unvaporized droplets, even those of very small size.

Finally, the present invention have appreciated that the above described objectives are most advantageously achieved with a device having a "draw" similar to that of a conventional smoking device, such as a cigarette. It is believed that users may rapidly become dissatisfied with a smoking substitute that requires too little or, more particularly, too much inhalation effort for the sensation achieved. Similarly if the device dispenses too high a nicotine dosage with each puff, the user may receive more nicotine than desired and may be forced to change smoking habits. Either of these alternatives is undesirable in that the user will be less willing to substitute the smokeless substitute if the "familiar feeling" is compromised or if the substitute is somehow less pleasurable.

In addition to U.S. Pat. No. 4,284,089 mentioned earlier herein, others have described nicotine dispensing devices. U.S. Pat. No. 4,393,884, for example, describes a demand inhaler holding a reservoir of pressurized nicotine and having a complicated mechanical system, all encased in a tube for oral nicotine input. U.S. Pat. No. 2,860,638 describes a tubular device for oral inhalation of substances such as nicotine. This device may contain filler material such as cotton or mineral matter in which substances such as nicotine may be absorbed.

U.S. Pat. No. 3,280,823 describes a tobacco smoke filter comprising an ion-exchange resin containing nicotine for nicotine enrichment of gases inhaled therethrough. U.S. Pat. No. 3,584,630 describes a filter section comprising nicotine weakly absorbed on carbon black for nicotine enrichment of inhaled gases.

U.S. Pat. No. 4,083,372 describes a cigarette-simulating inhaler with a fibrous wick of material such as cellulose acetate or cotton fibers and a puncturable capsule of flavorant for release into the wick prior to inhalation of air therethrough.

SUMMARY OF THE INVENTION

In accordance with a preferred embodiment of the present invention, a nicotine dispenser is described. This nicotine dispenser comprises a housing defining a passageway for air through the dispenser. Interposed in the passageway is at least one porous plug comprising a first polymeric substance, the first polymeric substance being able to absorptively and reversibly retain and release nicotine, and nicotine. The nicotine dispenser is preferably adapted to simulate a cigarette and deliver satisfactorily an inhaled dose of nicotine, without any tars or othre noxious products of tobacco combustion.

BRIEF DESCRIPTION OF THE DRAWINGS

Additional objects, features and advantages of the present invention will become apparent by referring to the following detailed description of the preferred embodiments in connection with the accompanying drawings, wherein like reference numerals refer to like elements throughout all the figures. In the drawings:

FIG. 1 is a perspective view which illustrates one embodiment of a nicotine dispenser constructed according to the present invention.

FIG. 2 is a cross-sectional view of one embodiment of an nicotine dispenser of this invention taken along line 2—2 of FIG. 1.

DESCRIPTION OF THE PREFERRED EMBODIMENTS

The nicotine dispenser of the present invention, as generally designated by the numeral 10 in FIG. 1 and FIG. 2, includes a tubular housing 12 defining a passageway 14 for air drawn through the dispenser 10, in a direction indicated by an arrow 16. The path of air drawn through the dispenser 10 may be in either direction. Interposed in the passageway 14 is a porous plug 18. This particular nicotine dispenser 10 is in a preferred shape, the elongated tube shape of a conventional cigarette. It should however be understood that other designs and forms are equally viable. The cigarette format illustrated by FIG. 1 is the most conventional configuration of the dispenser but not the only functionally effective form of the device.

The housing 12 may be made of a variety of materials. It is preferable that the housing 12 material is chemically inert and non-absorptive with respect to nicotine which is to be reversibly retained by the porous plug 18.

In the most preferred embodiment of this invention the housing 12 is manufactured with a diameter, length and weight which approximate that of a conventional cigarette.

Furthermore, the housing 12 is preferably provided with the appropriate color to present the same appearance as a conventional cigarette. In addition, a tipping band 20 made of paper, cork or other suitable material may be applied around the mouthpiece end 22 of the device 10 to simulate the appearance of the filter tip on a conventional cigarette.

The porous plug 18 comprises two materials: a first polymeric substance and nicotine. The first polymeric substance is able to absorptively and reversibly retain and release nicotine.

The term absorptively retaining nicotine as used herein is to be distinguished as meaning a physical retention as yet incompletely defined. The physical retention apparently involves a reversible penetration of nicotine into the first polymeric substance, the nicotine intercalating between polymeric chains.

A nicotine-bearing mixture or nicotine itself may be dispersed in and dispensed from the first polymeric substance. It has been found that a number of substances may be advantageously provided in the nicotine or nicotine mixture which is placed in the porous plug 18 of the present invention. Nicotine (d), nicotine (1), nicotine (d1) and possibly mixtures containing nicotine salts may all be used to advantage in the nicotine-bearing mixture of the present invention to provide the nicotine vapors which are inhaled by the user. A product obtained commercially from Eastman Company, Stock No. 1242, having 98% nicotine (1), has been used in one embodiment of the device and found to perform with satisfactory results. When the term "nicotine" is used herein, it unless otherwise defined, indicates usage of Eastman Company nicotine or that from any numerous commercial sources. Commercial nicotine is preferably distilled under vacuum to provide high purity nicotine for the dispenser 10 of the present invention.

Any number of nicotine-bearing mixtures are usable for emplacement in the porour plug 18 of the present invention. The specific nicotine-bearing mixture being used in a particular embodiment of the present invention is largely dependent upon the specific dispenser, its configuration and substances desired to be dispensed. In the most preferred embodiment of this invention, a number of other materials have been found to provide advantageous results when added to the nicotine bearing mixture. The commercial nicotine which is available in the marketplace is entirely a by-product of the tobacco industry. Extraction and purification procedures are generally well-known in the tobacco industry.

In the nicotine-bearing mixture, nicotine enhancing materials, organic acids and volatile carriers may be added and mixed in accordance with normal manufacturing procedures. It should be noted in selecting additive materials, that they must be suitable for human exposure and/or consumption. In particular, most chemicals may be theoretically toxic of their level of concentration is increased enough. Therefore, it is essential to select the materials for use in the formulation of this invention such that they can be used within accepted toxicity guidelines.

In addition to the above, a number of other materials such as menthol may for example be added to provide a desireable flavor when added to a nicotine-bearing mixture. Such flavorings may also be added in the form of synthetic ingredients.

Menthol may also be added to the mixture for a variety of reasons including flavoring or as a carrier material or to suit the particular taste of the user. The menthol which has been used in USP Leveratatery, obtained from the Gentry Corporation and may be dissolved in solvents such as ethanol or liquid nicotine to form a liquid. Menthol vapors are absorbed by a polyolefin porous plug 18 of the present invention.

Anti-oxidants such as butylated hydroxy toluene, butylated hydroxy anisole, propyl gallate or tertary butyl hydroxy quinone may also be added to the nicotine before or after impregnation into the porous plug 18. Such anti-oxidants, for example may be used to stabilize nicotine for a dispenser 10 with a longer shelf life.

Nicotine may be loaded into the porous plug by numerous means. For example, the porous plug may be contracted with liquid nicotine, with nicotine vapor or with a solution of nicotine. A solution of nicotine in supercritical liquid carbon dioxide is also thought to represent an advantageous way of introducing nicotine to porour plugs 18. Porous plugs 18 may be impregnated with nicotine before or after their interposing placement in the passageway 14 of a dispenser 10.

A variety of flavoring materials may be conveniently added to a formulation of nicotine to provide a desired effect. As has been previously mentioned, well-known flavorants which are approved for human consumption can be used in specified amounts. The use of such flavor materials is not intended to be a limiting factor in this application, but rather, it is intended to recite several of the possibilities for enhancing the final nicotine formulation of this invention.

For the purpose of the present invention the first polymeric substance should be reersibly absorptive to nicotine so that nicotine is absorbable and releasable. However, it is also important that the material be sufficiently absorbent of releasable nicotine to hold enough nicotine so that at least about 1 microgram is dispensed in response to each puff of the user with a dispenser 10 having a nicotine-loaded porous plug 18. The first polymeric substance is typically a material generically described as an olefinic polymer. More specifically, the first polymeric substance is preferably polyethylene or polypropylene but may also be any polyolefin or polyolefindiene such as polybutadiene, poly-1-butene, polyisobutylene, polyisoprene, poly-4-methyl pentene, or combustions thereof, for example. Of particular preference is formulating the porous plug 18 of the present invention is a high density polyethylene. Although amorphous rather than crystalline polyethylene appears to have a greater nicotine-absorptive capacity, porous plugs are more readily produced from high density polyethylene which has adequate capacity for reversible nicotine absorption. The porous plug may be produced mechanically and may also be a mass of filaments.

Polymeric substances such as polystyrene and polycarbonate are dissolved by nicotine and thus not usable in the practice of the present invention. Polymers containing halogens or nitrogen or sulfur, although they may be found to have the desired reversible nicotine absorptivity are not preferred becasue of their potential emission of noxious fumes upon accidental ignition.

In a preferred embodiment of the present invention, the housing 12 of the dispenser 10 is composed of a second polymeric substance. The second polymeric substance is preferably resistant to penetration by nicotine and produces no noxious fumes upon accidental ignition. A preferred second polymeric substance is oriented polybutyleneterephthalate.

The tipping paper comprising the band 20 of the dispenser 10 is preferably non-nicotine absorbent. Ordinary cigarette tipping paper may be advantageously treated to decrease its absorbent capacity for nicotine. Such treatment may comprise: exposure to ammonium hydroxide, dimethyldichlorosilane or polyvinylpyrrolidone, for example.

It is also preferred for preparation of packages containing the dispensers 10 of the present invention to wrap sets of said dispensers 10 in a wrapping nonabsorptive for and substantially nonpermeable to nicotine. A wrapping of biaxially oriented polyethylenetrephthalate film has been found to suitably retain nicotine in nicotine loaded dispensers 10 wrapped therein.

Many other embodiments of the present invention may be readily envisioned by those skilled in the art upon examination of this specification, including the following examples which are presented to fully describe many features of the invention.

EXAMPLE 1

Polyethylene Absorption from Liquid Nicotine

A low density polyethylene tube (obtained from Blackwell Plastics, Houston, Texas) weighing 721.2 mg was immersed in liquid nicotine (98%, Eastman Kodak) for 17 hr at 75° F. The tube was withdrawn from the nicotine, washed with water and dried. The dried tube weighed 743.5 mg. The net increase in weight was 22.3 mg, which indicated that low density polyethylene may absorb nicotine to form a composite with about 3% nicotine. Although it was noted that the dried tube was tactually dry, an odor of nicotine was emitted by the tube-nicotine composit.

EXAMPLE 2

Attempted Extraction of Nicotine from a Nicotine Containing Polyethylene Tube

A low density polyehtylene tube (8×84 mm) weighing 743.5 mg and containing 22.3 mg of absorbed nicotine was immersed in 0.1M hydrochloric acid at ambient temperature for periods of 1 minutes and 10 minutes. After washing, drying and weighing, the 1 min. HCl immersion was found to have caused a weight loss of 0.4 mg and the 10 min. immersion a weight loss of 1.4 mg. This experiment suggested that, should a nicotine containing polyethylene sample be ingested, that the internal emission of nicotine would be slow rather than immediate. It was also indicated that nicotine had deeply penetrated the polyethylene rather than being absorbed or superficially absorbed.

EXAMPLE 3

Polyethylene Absorption of Vaporous Menthol

A low density polyethylene tube (8×84 mm) weighing 824.3 mg was sealed in a test tube with menthol crystals. The test tube was then placed in an oven at 125° F. for 2 hr. The tube was removed from the test tube, washed with ethanol, dried and weighed. The tube then weighed 865.4 mg, showing a weight increase of 41.1 mg ascribable to absorbed menthol. This experiment indicates that menthol, as well as nicotine may be absorbed by polyethylene.

EXAMPLE 4

Polyethylene Film Absorption from Liquid Nicotine

Two types of polyethylene film (1 mil thickness) from Phillips Petroleum, Bartlesville, OK were obtained: NO. TR140, a blown film of high crystallinity; and No. OX611, a cast film of low crystallinity. Samples of both film types were weighed and immersed in nicotine (98% Eastman Kodak, Rochester, N.Y.) at 25° C. for 5 hours. After withdrawal from the nicotine, the film samples were carefully wiped until completely free of liquid, and weighed. The results of this immersion are shown in Table 1.

TABLE 1

Nicotine Absorption by Polyethylene Film

| Sample | Preliminary Weight | Postimmersion Weight | Nicotine Absorbed | % Nicotine (of original wt.) |
|---|---|---|---|---|
| TR140 | 84.9 mg | 86.8 mg | 1.9 mg | 2.2% |
| OX611 | 128.9 mg | 133.7 mg | 4.8 mg | 3.7% |

As the data in Table 1 indicates both types of polyethylene film absorb nicotine, the low crystallinity polyethylene absorbing nicotine more efficiently.

EXAMPLE 5

Absorption of Nicotine Vapor by Various Polymers

Valox (polybutyleneterephthalate) in various forms was obtained from General Electric (Polymer Products Department). Tedlar (polyvinylfluoride film) was obtained from DuPont de Nemours & Company. Gafphite 1600A (polybutyleneterephthalate) was obtained from General Aniline Fiber. PPh (polyropylene homopolymer) was obtained from Teel Plastics, Baraboo, Wisconsin. Various preweighed samples (from 40 mg to about 800 mg in weight) of these polymers were incubated in sealed containers with a nicotine saturated air for different times and at different temperatures and again weighed. The results of these manipulations are shown in Table 2.

TABLE 2

Percent Weight Gain For Various Polymers Subjected to Nicotine Vapors

| Sample | Temperature | Time (Days) | Weight Gain (wt. %) |
|---|---|---|---|
| Valox (10% glass filled) | ambient | 12 | 1.46 |
| Valox (10% glass filled) | 125° F. | 12 | 0.67 |
| Valox (40% glass filled) | ambient | 12 | 0.09 |
| Valox (40% glass filled) | 125° F. | 12 | 0.02 |
| Valox 310-083 | ambient | 7 | 0.08 |
| Valox 310-083 | 125° F. | 7 | 0.29 |
| Valox 310-095 | ambient | 7 | 0.10 |
| Valox 310-095 | 125° F. | 7 | 0.98 |
| Gafphite 1600A | ambient | 7 | 0.072 |
| Gafphite 1600A | 125° F. | 7 | 0.35 |
| Tedlar | ambient | 7 | 0.055 |
| Tedlar | 125° F. | 7 | 1.00 |
| PPH | 60° C. | 1 | 1.2 |
| PPH | 60° C. | 3 | 3.7 |
| PPH | 60° C. | 5 | 5.7 |
| PPH | 60° C. | 10 | 6.0 |
| PPH | 60° C. | 20 | 6.8 |
| PPH | 50° C. | 1 | 0.4 |
| PPH | 50° C. | 3 | 0.8 |
| PPH | 50° C. | 5 | 1.9 |
| PPH | 50° C. | 10 | 2.7 |
| PPH | 50° C. | 20 | 4.1 |
| PPH | 25° C. | 1 | 0.05 |
| PPH | 25° C. | 3 | 0.15 |

TABLE 2-continued

Percent Weight Gain For Various Polymers Subjected to Nicotine Vapors

| Sample | Temperature | Time (Days) | Weight Gain (wt. %) |
|---|---|---|---|
| PPH | 25° C. | 5 | 0.20 |
| PPH | 25° C. | 10 | 0.25 |
| PPH | 25° C. | 20 | 0.5 |
| PPH | 5° C. | 1 | 0.05 |
| PPH | 5° C. | 3 | 0.08 |
| PPH | 5° C. | 5 | 0.10 |
| PPH | 5° C. | 10 | 0.10 |
| PPH | 5° C. | 20 | 0.15 |

As the data in Table 2 indicates, under comparable conditions, (polypropylene at 50° C. for 10 days and polybutylene terephthalate or polyvinylfluoride at 125° F. for 7 days), that the polyolefin polypropylene is much more effective as a nicotine absorbent (2.7 wt. % gain) than is the polybutylene terephthalate (less than 1%) or polyvinyl fluoride (about 1%). Also, these results suggest the usability of such relatively nonabsorptive polymers for portions of the presently described nicotine dispenser 10 where nicotine non-absorption is desirable such as the housing 14 or wrapping (not shown).

EXAMPLE 6

Absorption and Desorption of Nicotine Vapors By Low Density Polyethylene Tubes

Preweighed low density polyethylene tubes (Blackwell Plastics, Houston, Texas) were subjected to nicotine vapors from a predetermined amount of nicotine in a sealed tube at a temperature of about 125° F. for 24 hours. The weight gain of the tubes were determined and the results are shown in Table 3.

TABLE 3

Polyethylene Sample Absorption Of Nicotine Vapors

| | Polyethylene or Nicotine Weight | |
|---|---|---|
| | Sample 1 | Sample 2 |
| Sample wt. before exposure | 1.0159 g | 1.0177 g |
| Nicotine available | 22.0 g | 25.6 mg |
| Sample wt. after exposure for 24 hrs. | 1.0350 g | 1.0387 g |
| Nicotine absorbed | 19.1 mg | 21.0 mg |

Sample 1 and Sample 2 were then exposed to ambient air for various periods of time and periodically weighed to determine loss of absorbed nicotine. The measurements of nicotine desorption are shown in Table 4.

TABLE 4

Polyethylene Desorption of Absorbed Nicotine

| | Decrease in Sample Weight (Nicotine Loss) | |
|---|---|---|
| Time | Sample 1 | Sample 2 |
| 1 hr | 0.9 mg | 0.4 mg |
| 2 hr | 1.6 mg | 1.3 mg |
| 4 hr | 3.3 mg | 3.1 mg |

After a 4 hr. exposure to ambient air, over a 10% loss in absorbed nicotine was noted. This indicates the reversible nature of nicotine absorption in this particular polyolefin, similar to that qualitatively noted with other polyolefins.

EXAMPLE 7

Polyethylene and Teflon Absorption from Liquid Nicotine and Desorption of Nicotine Vapors from the Polyethylene A low density polyethylene tube weighing 753.3 mg and a Teflon cylinder weighing 14.4983 g were immersed in liquid nicotine for 3 hr at 120° F. After withdrawal and removal of superficial nicotine, the polyethylene sample showed an increase in weight of 48.1 mg and the Teflon sample showed a decrease in weight of 0.8 mg. The polyethylene sample was then exposed to ambient air for three days and exhibited a weight loss of 27.0 mg (about 56% loss of absorbed nicotine). The suitability of polyethylene as a nicotine reservoir for a nicotine dispenser in further demonstrated by the above data, as well as the nicotine non-absorptivity of Teflon.

EXAMPLE 8

Polypropylene Absorption from Liquid Nicotine and Desorption Under Vacuum

Four polypropylene samples obtained from Teel, Baraboo, Wisconsin, were washed, dried, weighed and immersed in liquid nicotine for 21 hrs at 120° F. The samples were withdrawn, washed with water, dried and weighed again to determine the extent of nicotine absorption in the nicotine-loaded samples. These nicotine-loaded polypropylene samples were then placed in a vacuum dessicator, subjected to a vacuum of about 75 mm of pressure for 10 min. and reweighed to determine loss of absorbed nicotine. The results of these manipulations are shown in Table 5.

TABLE 5
Polypropylene Absorption from Liquid Nicotine and Desorption Under Vacuum

|  | 1 | 2 | 3 | 4 |
|---|---|---|---|---|
| Sample weight (mg) | 428.5 | 429.3 | 511.0 | 623.4 |
| Sample weight after immersion | 443.8 | 455.6 | 540.5 | 640.7 |
| Nicotine absorbed (mg) | 15.3 | 31.7 | 29.5 | 17.3 |
| % nicotine of sample weight | 3.6 | 7.5 | 5.8 | 2.8 |
| Sample weight after 10 min. under vacuum | 443.4 | 454.5 | 539.9 | 640.6 |
| Mg nicotine desorbed under vacuum | 0.4 | 1.1 | 0.6 | 0.1 |

As the above data indicaet, polypropylene is an effective nicotine absorbent and absorbed nicotene does not flash evaporate when subjected to a vacuum which would quickly evaporate free nicotine liquid. This again indicates more than adsorption or superficial absorption, such as in surface crevices.

EXAMPLE 9

High Density Porous Polyethylene Absorption of Nicotine Vapors

Four samples (cylinders with about a ¼ inch diameter and 1 ½ inch length) of porous high density polyethylene were obtained from Porex Technologies (Fairburn, GA). These samples were weighed and then each incubated at ambient temperature in a sealed tube and in the presence of 40–50 mg nicotine. The weight of the samples were periodically determined and the resultant data shown in Table 6.

TABLE 6
Nicotine Weight Gain of Porous High Density Polyethylene

| | | Original Sample No. | | | |
|---|---|---|---|---|---|
| | | 1 | 2 | 3 | 4 |
| | | Weight (mg) | | | |
| | | 689.3 | 692.0 | 699.3 | 694.3 |
| | Incubation | Increase in weight (mg) | | | |
| | Temp. | ambient | ambient | 120° F. | 120° F. |
| Incubation Time | 1 hr | 1.0 | 1.0 | 3.5 | 4.2 |
| | 2 hr | 1.5 | 1.7 | 3.6 | 5.9 |
| | 1 day | 6.2 | 6.1 | 12.9 | 13.6 |
| | 6 days | 11.3 | — | 17.7 | — |

The data in Table 6 demonstrates the absorptive ability of high density porous polyethylene for nicotine vapors.

EXAMPLE 10

Vaporization of Nicotine from a Nicotine-Loaded Porous Polyethylene Plug

A 360 mg piece of Porex high density porous polyethylene was interposed in the passageway of an aluminum tube. The aluminum tube was 84 mm long, had an outer diameter of 5/16 inch and a wall thickness of 5/1000 inch. the porous plug was contacted with about 18 mg of liquid nicotine which was promptly absorbed to form a porous plug containing about 5% by weight nicotine. Puffs of air (35 cc/puff) were drawn through the tube and nicotineloaded porous plug at about 1050 cc per minute (2 sec/puff). The nicotine content of the air puffs was monitored by gas chromatography (Model 5880A, Hewlett Packard).

Table 7 contains the data concerning nicotine in the air puffs.

TABLE 7
Nicotine Vaporized From A Porous Nicotine-Loaded Polyethylene Plug

| Time | Number Puffs | Micrograms Nicotine Per Puff |
|---|---|---|
| 10:31 | 1 | 8.2 |
| 10:33 | 74 | 8.1 |
| 10:36 | 147 | 6.7 |
| 10:40 | 220 | 5.6 |
| 10:43 | 292 | 5.2 |
| 10:46 | 365 | 4.7 |
| 10:49 | 438 | 4.2 |
| 10:52 | 511 | 3.8 |
| 10:55 | 584 | 3.2 |
| 10:58 | 657 | 2.9 |

The total nicotine in the puffs was 3423 micrograms or about 19% of the nicotine originally loaded into the porous plug. The temperature was about 25° C. for these manipulations.

EXAMPLE 11

Attempted Extraction with Ethanol of Nicotine from a Porous Polyethylene Plug An aluminum tube with an interposed porous high density polyethylene plug (Porex Technologies) was constructed as described in Example 10 except that the plug was loaded with 20 mg of liquid nicotine. A 35 cc volume of 95% ethanol was drawn through the loaded plug in a 3 second period and then analyzed for nicotine content. The volume of 95% ethanol, an excellent nicotine solvent under normal conditions, contained 1.4 mg of nicotine, this being about 7% of the absorbed nicotine. These data illustrate that rapid extraction of nicotine from a state of polyethylene absorption is not easily accomplished and that the nicotine had penetrated the polyethylene.

EXAMPLE 12

Absorption of Nicotine Vapors by Several Materials at Different Temperatures

Preweighed samples of various materials were sealed in tubes with excess nicotine vapors. After various periods of time at different temperatures the samples were removed and reweighed. Increases in sample weight were calculated as weight percent (wt %) increases based upon the original sample weights.

Tip paper number MR-320 was obtained from the Schweitzer Paper Company, Division of Kimberly Clark, Neenah, Wisconsin. Kimdura, a polypropylene trilaminate, was also obtained from Kimberly Clark. A polypropylene tube (PPT) was obtained from Teel Plastics, Baraboo, Wisconsin and polypropylene fiber (PPF) Type 701 from Hercules Plastics, Wilmington, Delaware. The absorption of nicotine by these samples, as shown in wt% increases is presented in Table 8.

TABLE 8

| | | Absorption of Nicotine Vapor | | | |
|---|---|---|---|---|---|
| | Temp | wt % nicotine | | | |
| Sample | (°C.) | 1 day | 3 day | 5 day | 10 day | 20 day |
| Tip Paper | 5 | 1.8 | 2.5 | 1.9 | 3.6 | 2.7 |
| | 25 | 0.78 | 1.3 | 1.9 | 3.0 | 4.1 |
| | 20 | 4.0 | 7.4 | 7.5 | 6.4 | 13.0 |
| | 60 | 5.1 | 14.0 | 7.1 | 12.0 | 18.0 |
| Kimdura | 5 | 1.3 | 0.08 | 0.08 | 0.31 | 0.28 |
| | 25 | 0.11 | 0.16 | 0.33 | 0.30 | 0.58 |
| | 50 | 0.82 | 1.1 | 1.3 | 1.6 | 2.5 |
| | 60 | 1.3 | 3.0 | 3.5 | 4.2 | 6.2 |
| PPT | 5 | 0.03 | 0.07 | 0.08 | 0.11 | 0.14 |
| | 25 | 0.06 | 0.18 | 0.18 | 0.27 | 0.52 |
| | 50 | 0.40 | 0.74 | 1.9 | 2.7 | 4.1 |
| | 60 | 1.2 | 3.7 | 5.7 | 6.0 | 6.0 |
| PPF | 5 | 0.06 | 0.05 | 0.002 | 0.11 | 0.22 |
| | 25 | 0.07 | 0.12 | 0.24 | 0.15 | 0.64 |
| | 50 | 0.75 | 1.5 | 1.7 | 1.2 | 3.6 |
| | 60 | 1.6 | 3.2 | 5.1 | 2.9 | 8.7 |

As shown by the data in Table 8 tip paper, tirlaminate polypropylene, polypropylene tube and polypropylene fiber all absorb nicotine vapors and that this absorption is proportional to time and temperature. These observations further are applicable to a choice of materials for a nicotine dispenser, for example, tip paper will absorb nicotine and thus preferably, if used at all, should be treated so it does not effectively absorb nicotine in a fashion so it is not readily deliverable by a nicotine dispenser. Additionally, a nicotine dispenser with a polypropylene tube housing of the type studied above, may likewise result in the nicotine being absorbed in the housing by a fashion not readily deliverable to the user.

EXAMPLE 13

Desorption of Nicotine Vapors from a Porous Polyethylene Plug

A 360 mg porous polyethylene plug was interposed in a tubular aluminum housing as described in Example 10. The porous plug was loaded by contact with different amounts of nicotine to form an interposed porous plug containing a particular weight percent (wt%) nicotine. Air puffs were drawn through the tube and nicotine emitted and monitored as described in Example 10.

The puffs were continued at ambient temperature until the nicotine emission per puff first reached a level below 3 micrograms of nicotine. The puffing was then terminated and total emitted nicotine calculated. The data resulting from this test is shown in Table 9.

TABLE 9

| wt % nicotine | total mg nicotine loaded | maximum nicotine per 35 cc puff (micrograms) | no. of puffs before content is below 3 micrograms per puff | total mg nicotine emitted |
|---|---|---|---|---|
| 2 | 7.2 | 8.9 | 365 | 2.3 |
| 3 | 10.8 | 7.5 | 730 | 3.8 |
| 4 | 14.4 | 8.3 | 511 | 2.7 |
| 5 | 18.0 | 8.2 | 657 | 3.4 |
| 6 | 21.6 | 9.9 | 948 | 5.4 |
| 7 | 25.2 | 9.7 | 1895 | 11.1 |
| 8 | 28.8 | 11.3 | 2187 | 16.5 |

The data in Table 9 shows, a nicotine dispenser configuration of this type, preferably delivering at least 500 puffs containing from three to ten micrograms of nicotine per puff, should contain a porous polyethylene plug of at least about 3% nicotine or about 10.8 mg nicotine. The dosage of nicotine per puff from a nicotine dispenser is most preferably less than 10 micrograms but more than 5 micrograms, although a dosage between 2.5 micrograms and 12 micrograms is acceptable. Preferred typical temperates and flow rates for usage of a nicotine dispenser 10 of the present invention preferably range from 0° C. to 40° C. and flow rates from 100 cc/min to 2000 cc/min.

EXAMPLE 14

Absorption of Nicotine Vapors by a Selection of Papers and Treated Papers

A variety of paper samples potentially usable as tipping papers for a tubular nicotine dispenser were testsed for nicotine absorption. Samples were washed either with water or with 5% aqueous ammonium hydroxide dried and weighed. The paper samples were then subjected to nicotine vapors in a sealed tube at 50° C. for 6 ½ days and reweighed. Paper samples were obtained from Schweitzer Paper Company, a Division of Kimberly Clark. The results of these tests are shown in Table 10.

TABLE 10

| | Paper Absorption of Nicotine Vapors | |
|---|---|---|
| | wt % nicotine | |
| Paper Sample | water washed | 5% NH$_4$OH washed |
| WTA-33 gsm | 2.2 | 2.4 |
| Abrol 10#500 | 2.1 | 1.1 |
| GSR156-HO-34 gsm | 2.4 | 4.1 |
| MR320 Maretip | 2.2 | 2.7 |
| GSR-236-M2-36HD | 2.4 | 1.7 |
| GSR-236-M1-36HD | 1.9 | 2.0 |
| MR320 Maretip (Printed version) | 4.2 | 3.7 |

The above data indicates that, for at least some papers, treatment with 5% aqueous ammonium hydroxide decreases nicotine absorption capacity.

EXAMPLE 15

Polypropylene Absorption from Liquid Nicotine Time and Temperature Dependency

Polypropylene homopolymer tubes (Teel Plastics) were weighed and immersed in liquid nicotine. After withdrawal, the tubes were washed, dried and weighed. Increases in weight were utilized to calculate wt% absorption. Table 11 shows data obtained from these manipulations.

TABLE 11

Polypropylene Nicotine Absorption

| Time (hr) | wt % absorption, at | | | |
|---|---|---|---|---|
| | 5° C. | 25° C. | 50° C. | 60° C. |
| 1 | 0.007 | 0.014 | 0.37 | 0.87 |
| 25 | 0.016 | 0.085 | 5.4 | 6.9 |
| 88 | 0.008 | 0.47 | 5.9 | 6.4 |
| 192 | 0.028 | 0.87 | 6.0 | 6.5 |

The data in Table 11 shows that polypropylene effectively absorbs liquid nicotine in a manner dependent on time and temperature.

EXAMPLE 16

Packaging Materials Test

Samples (3 in$^2$) of Van Leer microporous polypropylene film were each weighed and loaded with 40 mg of nicotine. The nicotine-loaded samples were heat-sealed in pouches formed from 12 in$^2$ packing film. Packaging films included PET (polyethyleneterephthalate); PP (polypropylene); and aluminum metallized PET. After incubating the sealed pouches of nicotine for 2 weeks at 125° F., the microporous polypropylene film samples were removed and weighed. Table 12 shows the data resulting from the above manipulations in terms of the percentage of nicotine lost during the 2 week period.

TABLE 12

Nicotine Permeability of Packaging Materials

| Packaging Film | % Nicotine Lost |
|---|---|
| I.C.I. Melinex 470 (PET) | 31 |
| I.C.I. Melinex 475 (PET) | 42 |
| Bemis Esterphane (PET) | 5 |
| Bemis Propa Film (Polypropylene) | 99 |
| I.C.I. Melinex Metalized 850 (PET/Aluminum) | 40 |
| I.C.I. Melinex 850 (PET) | 31 |
| Kimberly Clark KimDura (Polypropylene) | 99 |
| Bemis Metalized Esterphane (PET/Alum) | 5 |

As indicated by the above data, polypropylene film would be unsatisfactory for packaging nicotine dispensers while certain biaxially oriented polyethyleneterephthalate film or metallized polyethyleneterephthalate film appears to effectively retard nicotine evaporation.

Further modifications of the present invention will be apparent to those skilled in the art who have had the benefit of this disclosure. Such modifications however lie within the spirit and scope of the invention as defined by the following claims.

What is claimed is:

1. A nicotine dispenser for non-pyrolytic use, adapted to release nicorine-bearing vapor into air drawn through the dispenser, said dispenser comprising:
   (a) a housing, said housing defining a passageway for air through the dispenser; and
   (b) interposed in the passageway, at least one porous plug comprising nicotine and a first polymeric substance, the first polymeric substance being able to absorptively and reversibly retain and release the nicotine,.

2. The nicotine dispenser of claim 1 wherein said housing is shaped as an elongated tube.

3. The nicotine dispenser of claim 2 wherein said elongated tube includes a first portion adapted to retain at least one porous plug and a second portion adapted to be a mouthpiece.

4. The nicotine dispenser of claim 3 wherein the second portion is defined further as having a band of generally cork-colored paper.

5. The nicotine dispenser of claim 4 wherein the cork-colored paper is defined further as having been subjected to a treatment to reduce nicotine absorbtivity.

6. The nicotine dispenser of claim 5 wherein the treatment is defined further as comprising exposure to ammonium hydroxide, dimethyldichlorosilane or polyvinylpyrrolidone.

7. The nicotine dispenser of claim 1 wherein the first polymeric substance consists essentially of a polyolefin.

8. The nicotine dispenser of claim 1 wherein the first polymeric substance consists essentially of polyethylene, polypropylene, polybutadiene, poly-1-butene, polyisobutylene, polyisoprene, poly-4-methyl-1-pentene or combinations thereof.

9. The nicotine dispenser of claim 1 wherein the first polymeric substance is polyethylene or polypropylene.

10. The nicotine dispenser of claim 1 wherein the first polymeric substance is high density polyethylene.

11. The nicotine dispenser of claim 1 wherein the housing comprises a second polymeric substance and the second polymeric substance is resistant to penetration by nicotine.

12. The nicotine dispenser of claim 11 wherein the second polymeric substance is polybutyleneterephthalate.

13. The nicotine dispenser of claim 1 wherein the porous plug comprises a molded unit.

14. The nicotine dispenser of claim 1 wherein the porous plug comprises a shaped mass of filaments.

15. The nicotine dispenser of claim 1 wherein also interposed in the passageway is a second porous plug, the second porous plug being resistant to the absorption of nicotine.

16. The nicotine dispenser of claim 1 wherein at least one porous plug comprises a vaporizable flavorant such as menthol or tobacco extract.releasable into air drawn through the dispenser.

17. The nicotine dispenser of claim 1 wherein the nicotine is defined further as being accompanied by an antioxidant.

18. The nicotine dispenser of claim 17 wherein the antioxidant is butylated hydroxyanisole propyl gallate, tertiary butylhydroxy-quinone butylated hydroxytoluene or mixtures thereof.

19. The nicotine dispenser of claim 1 wherein the porous plug comprising nicotine is defined further as containing between about 1 mg and about 25 mg nicotine.

20. The nicotine dispenser of claim 1 wherein the porous plug is defined further as releasing as a vapor between about 2.5 micrograms nicotine and about 12 micrograms nicotine when 35 cc of air are drawn through the dispenser at a temperature between about 0° C. and about 40° C. and at a flow rate between about 100 cc/min and about 2000 cc/min.

21. The nicotine dispenser of claim 1 wherein the porous plug is defined further as having been loaded with nicotine by contact with liquid nicotine, by exposure to nicotine vapor, or by contact with nicotine in a volatile liquid solvent.

22. Tobacco-free tubular non-pyrolytic nicotine dispensers comprising nicotine reversibly contained within an emplaced porous polymeric plug, said dispensers being packaged in a sealed film of oriented polyethylene terephthalate.

23. A composition consisting essentially of a solid polyolefin with from about 1 weight percent to about 10 weight percent nicotine absorbed therein.

24. The composition of claim 23 wherein the polyolefin is polyethylene or polypropylene.

25. A method of making a nicotine dispenser comprising:
provided a tubular housing resistant to absorption of nicotine and defining a passageway for air;
interposing in said passageway a porous plug comprising a polyolefin absorptive for nicotine; and exposing the porous plug to nicotine to load the porous plug with nicotine.

26. The method of claim 25 wherein the polyolefin is polyethylene or polypropylene.

27. The method of claim 25 wherein the polyolefin is high-density polyethylene.

28. A device simulating a cigarette for orally inhaling nicotine without tobacco combustion, the device comprising:
a tubular housing substantially chemically inert to nicotine and substantially non-absorptive of nicotine, said housing defining a passageway and being adapted at one end to be held in the mouth of a person; and
a source of absorptively retained nicotine interposed in said passageway, said source being capable of releasing nicotine into air inhaled through the passageway.

29. The device of claim 28 wherein the source comprises polyethylene or polypropylene.

30. A device for orally inhaling nicotine without combustion of tobacco, the device comprising:
a tubular housing, substantially non-sorbent toward nicotine and adapted at one end to be held in the mouth of a person; and
a source of absorptively-retained nicotine capable of releasing nicotine into air drawn through said housing, said source comprising a porous solid-form polyolefin.

31. The device of claim 30 wherein the source comprises polyethylene or polypropylene.

32. A device for the non-pyrolytic inhalation of nicotine, the device comprising:
a tubular member adapted at one end to be held in the mouth for inhalation of air therethrough; and
a quantity of porous solid-form polymer interposed in said member said polymer containing absorptively retained nicotine and being capable of releasing between about 2.5 micrograms and about 12 micrograms of nicotine into a 35 cc puff of air drawn through said member.

33. The device of claim 32 wherein the polymer is a polyolefin.

34. The device of claim 32 wherein the polymer is a polyethylene.

35. The device of claim 32 wherein the 35 cc puff of air is drawn through at a rate of about 1050 cc per minute.

36. A method of making a non-pyrolytic nicotine inhalant device, the method comprising: positioning in a tubular housing a portion of a nicotine-containing, porous, solid-form polymeric nicotine absorbent adapted to release nicotine upon he passage of air through said tubular housing.

37. The method of claim 36 wherein the polymeric nicotine absorbent comprises a polyolefin.

38. The method of claim 36 wherein the polymeric nicotine absorbent comprises polyethylene or polypropylene.

39. The method of claim 36 wherein the passage of air through said tubular housing is also through the porous solid form polymeric nicotine absorbent.

* * * * *